US006511442B1

(12) United States Patent
Lathan et al.

(10) Patent No.: US 6,511,442 B1
(45) Date of Patent: Jan. 28, 2003

(54) SYSTEM FOR EVALUATING AND PROMOTING DEVELOPMENT IN PERSONS WITH SEVERE DISABILITIES

(75) Inventors: Corinna E. Lathan, Wheaton, MD (US); Micheal Tracey, Arlington, VA (US); Adrian Blanarovich, Washington, DC (US)

(73) Assignee: The Catholic University of America, Washington, DC (US)

( * ) Notice: Subject to any disclaimer, the term of this patent is extended or adjusted under 35 U.S.C. 154(b) by 0 days.

(21) Appl. No.: 09/518,194

(22) Filed: Mar. 3, 2000

(51) Int. Cl.[7] .................................................. A61B 5/103
(52) U.S. Cl. ..................................................... 600/595
(58) Field of Search ................................. 600/544, 545, 600/546, 547, 587–595; 180/6.2–6.7; 901/30–39, 2–13; 434/112–117

(56) References Cited

U.S. PATENT DOCUMENTS 5,260,869 A    11/1993   Ferrier et al.
6,302,226 B1 * 10/2001   Kanno et al. ................ 180/6.5
6,349,231 B1 *   2/2002   Musha ....................... 600/544

* cited by examiner

*Primary Examiner*—Max F. Hindenburg
*Assistant Examiner*—Pamela Wingood
(74) *Attorney, Agent, or Firm*—Jagtiani + Guttag

(57) ABSTRACT

A novel system for augmenting human function using personal augmentation devices (PADs), controlled by physiological signals for the purpose of navigating and manipulating the external environment is provided. The system utilizes a variety of sensors connected to a data acquisition box (DAQ) to detect movement of a user. The DAQ, which is comprised of a microprocessor, will control the PAD according to the sensed user movement, thus mapping user input to user output. Controlling of the PAD provides important feedback to the user concerning manipulation of their external environment. In one embodiment, feedback concerning movement of the PAD is provided using a virtual reality system. This system allows people with severe disabilities to remotely interact with their environment using a PAD, thereby unlocking cognitive abilities, promoting curiosity, and providing sense of entitlement to explore, as well as allowing development to continue. A feature of this system is to map the user's inputs with outputs as a function of feedback. Users will then be able to learn input-output mappings based on the level of their physical control.

7 Claims, 9 Drawing Sheets

SYSTEM FOR EVALUATING AND PROMOTING DEVELOPMENT IN PERSONS WITH SEVERE DISABILITIES

CROSS-REFERENCE TO RELATED APPLICATIONS

This application makes reference to the following co-pending Provisional U.S. App. No. 60/122,989, entitled "A System and Method for Evaluating and Promoting Development in Persons with Severe Disabilities through an Exploratory Agent," filed Mar. 5, 1999. This application is hereby incorporated by reference.

BACKGROUND OF THE INVENTION

1. Field of the Invention

The present invention relates generally to interactive computer systems, and more particularly to a system for augmenting human functions for persons with disabilities. Even more particularly, the present invention relates to a system for remotely exploring and interacting with an environment, especially for persons with disabilities.

This invention is made with government support under contract number IIS-9813548, awarded by the National Science Foundation. The government may have certain rights in this invention.

2. Description of the Prior Art

The importance of play on children's cognitive and motor development has long been realized. Development is considered to be strongly dependent on learning through observation and direct manipulation of one's environment. This realization has been the basis of several virtual reality rehabilitation applications for children. Giving children control of their environment is a key functional goal in the clinical delivery of assistive technology. For example, powered mobility vehicles allow disabled children to experience movement and control and can facilitate their social, cognitive, perceptual, and functional development.

The most commonly used power mobility vehicle is a motorized wheelchair. There are drawbacks to the use of powered mobility vehicles. For example, it is not always apparent that the user can benefit from powered mobility, because the activity and effort of propelling a wheelchair for any length of time depletes the energy of these individuals. In addition, the use of powered mobility vehicles compromises productivity in other areas of life. Also, for children with severe motor disabilities, it is difficult to establish an appropriate control interface given existing assistive technology.

Studies have shown that the interactivity and three-dimensionality of a virtual reality environment is enormously beneficial to spatial learning by disabled children. The result of experiments that investigated transfer of spatial skills between different virtual environments confirmed that the skills disabled children acquired using virtual reality environments improved with exposure to successive environments. A control experiment compared three-dimensional and two-dimensional exploration, finding the former to be superior.

To overcome these problems and to take advantage of the results of previous experiments, a system that allows the user to interact with his environment needs to be developed. It would be preferable for this system to use a three-dimensional feedback mechanism, such as that provided by virtual reality, rather than, using a conventional computer monitor or other two-dimensional feedback mechanism. Applicants are not aware of any commercially viable systems that provide these features.

SUMMARY OF THE INVENTION

It is therefore an object of the present invention to provide a personal augmentation device (PAD) which will be actuated by a computer-based system having the potential for being universal, portable, and modular.

It is another object of the invention to provide a system by which an operator may remotely explore and interact with an environment through the use of a remote exploration device that provides three-dimensional sensory feedback from the remote exploration device to the user through a feedback device.

It is yet another object of the present invention to utilize a computer-based system that provides children with motor disabilities with opportunities to navigate and manipulate their external environment. The system allows the children to tele-interact, thereby unlocking their cognitive abilities, promoting curiosity, and providing a sense of entitlement to explore, as well as foster cognitive development.

It is a further object to provide a computer system coupled to a simple, inexpensive sensor and interface technology for allowing a variety of mobility options to become available to a disabled individual, such as computer-control of a remote-controlled wheelchair, a remote-controlled car or robotic device.

It is yet a further object to provide a computer system coupled to a sensor and interface technology for allowing a variety of remote sensing, operating, and mobility options to become available to an individual who seeks to remain immobile or distant from the area being explored or operated upon, such as computer control of a remote-controlled car, weapon, surveillance drone, or other robotic device.

It is yet another object to provide a system that can be used to test and further develop the child's ability to control devices through control of the PAD.

According to one broad aspect of the present invention, there is provided a system comprised of an interface to enable interaction with a computer-based system using one or more customized sensors. The sensors output signals which are representative of user inputs to a microcontroller-based data acquisition box (DAQ). The DAQ uses software to map user inputs to control a personal augmentation device (PAD) and to assess and process user input. The PAD then acts on the environment for the user. The movement of the PAD is fed back to the user either two-dimensionally or using virtual reality. The user must interpret this information as being mapped to his/her inputs and continue to respond.

According to another broad aspect of the invention, there is provided a method of evaluating and training for the development of cognitive, functional and perceptual skills by detecting the input of a user with one or more sensors, and mapping the input of the user to controls of a personal augmentation device by a microcontrolled data acquisition box.

According to another broad aspect of the invention, there is provided a system for evaluating and training for the development of cognitive, functional and perceptual skills, the system comprising: one or more sensors for generating input data, data acquisition means for acquiring said input data, and mapping means for mapping said input data to controls of a personal augmentation device.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

The term "sensors" is defined as any device that interacts with the environment to measure or record a change in a characteristic of the environment. Examples of sensors include, but are not limited to: pressure sensors, force sensing resistors, rotary potentiometers, photo-sensors, accelerometers, modified EMG sensors, resistive bend sensors, capacitive proximity sensors, and switches.

The term "input devices" is defined as any physical device that is manipulated by a user to generate a signal to a central processing unit. Examples of input devices include, but are not limited to: a mouse, joystick, trackball, and vibratory and/or tactile embodiments of the above or other similar input devices. Additionally, input may be derived through devices that measure eye movement, breathing, electrical currents, and other products of human physiological responses.

The term "input port" is defined as a physical port for providing connectivity for data from one device to another. Examples of input ports include, but are not limited to: serial ports, parallel ports, SCCI ports, universal serial bus ports (USB), infra-red ports (IR) and high frequency ports.

The term "personal augmentation device" or "PAD" is defined as a device that augments user input to manipulate the environment of the user. Examples of personal augmentation devices include, but are not limited to remote-controlled cars, wheelchairs, and/or robots or other remotely controllable devices.

The term "virtual reality" or "VR" is defined as an interactive set of tools that fuse the user with the system. These tools allow the user to engage their environment in a unique way and use their imagination to interrogate the environment. VR allows the user to take advantage of the relationships between physical stimuli and the cognitive impact from this stimulus. Examples of VR devices included, but are not limited to virtual reality domes, virtual reality goggles, and heads-up displays.

Description

Figure 1:
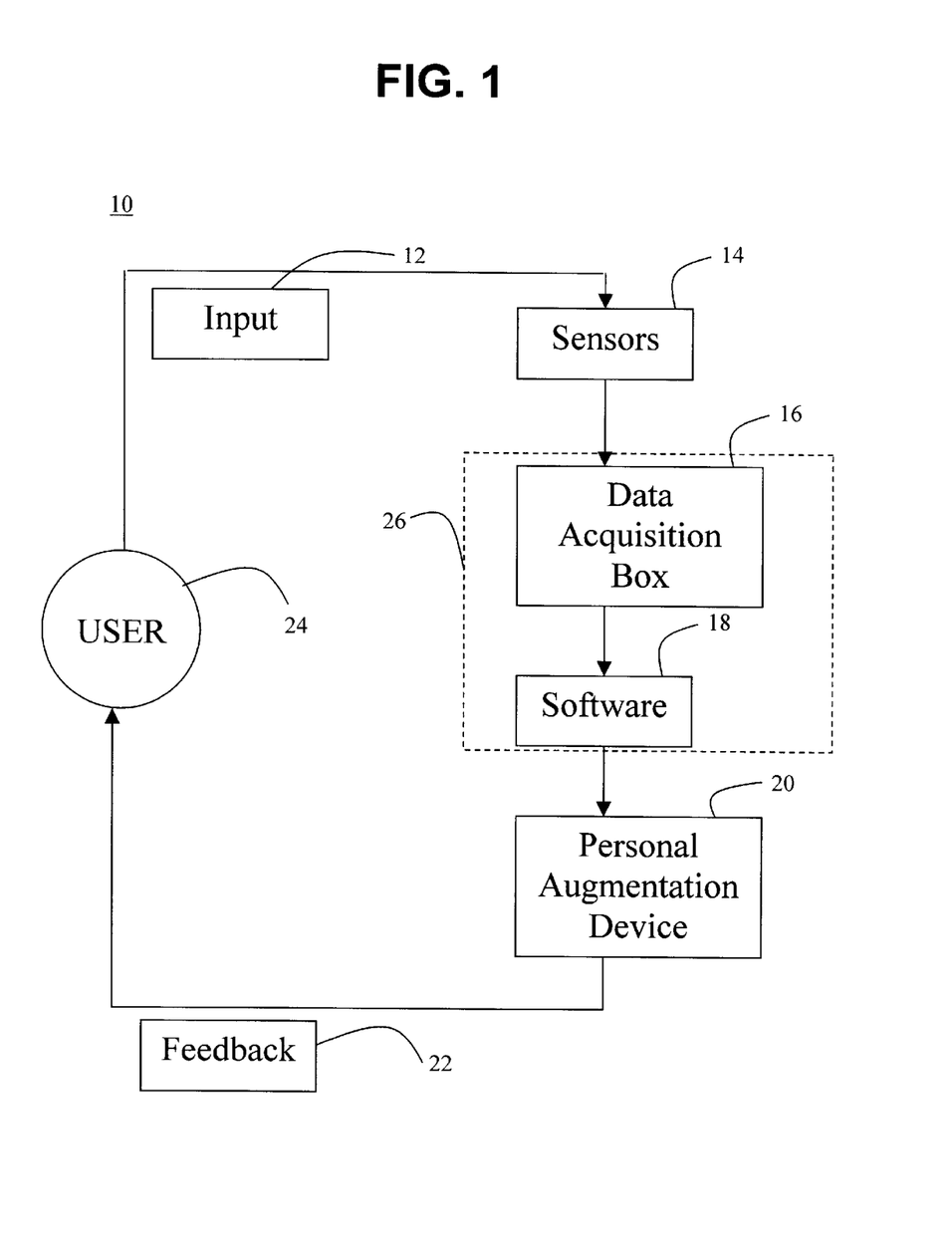
FIG. 1 is a block diagram of the system constructed in accordance with a preferred embodiment of the invention.

With reference to the Figures, wherein like references characters indicate like elements throughout the several views and, in particular, with reference to FIG. 1, a system and method for evaluating and promoting development in persons with severe disabilities is illustrated as element 10. The system comprises an input means 12, sensors 14, a data acquisition box 16, software 18, a personal augmentation device 20, and a feedback mechanism 22.

A user 24 interacts with system 10 through one or more customized sensors 14 or off-the shelf input devices 12 to enable interaction with a computer-based system 26. Sensors 14 were chosen and developed for the greatest range and flexibility in sensing capabilities. Examples of sensors include, but are not limited to: pressure sensors, force sensing resistors, rotary potentiometers, photo-sensors, accelerometers, modified EMG sensors, resistive bend sensors, capacitive proximity sensors, and basic switches. Off-the-shelf input devices 12 include, but are not limited to: a mouse, joystick, trackball or other similar input devices.

It should be appreciated that input devices 12 require the user 24 to have at least limited articulation, functionality or movement. It is preferable to utilize these input devices when appropriate. In other circumstances, the user 24 may have severely restricted articulation, functionality or movement. In this event, sensors 14 may be utilized as input to data acquisition box 16. Alternatively, sensors 14 may be used in conjunction with input devices 12 to teach motion control to user 24.

Now that the basic relationship between the user 24 and the input devices 12 and sensors 14 have been described, we will now address a novel sensing mechanism. In a preferred embodiment sensors 14 are comprised of electromyography (EMG) sensors, illustrated in FIG. 3A as element 28. EMG sensors 28 are used to detect muscle electricity or signal. However, conventional EMG sensors 28 use complicated expensive signal processing and circuitry to analyze the output of the EMG sensor. System 10 utilizes a novel detector circuit 30 to analyze the output of EMG sensor 28 at a low cost. As may be seen, detector circuit 30 comprises a high pass filter 32, a low pass filter 34, a comparator 36, a counter 38, and a frequency to voltage converter. Finally, an output analog signal 40 is generated.

Figure 7A:
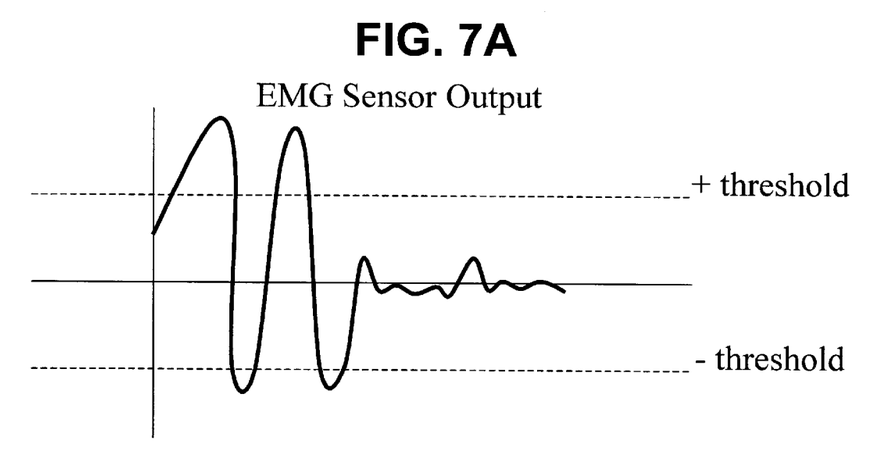
FIGS. 7A and 7B illustrate the output of an EMG sensor and counter that are used in the preferred embodiment of the invention.

To understand the functionality of detector circuit 30, the reader is referred to FIG. 7A that illustrates the output of EMG sensor 28. The voltage output of EMG sensor 28 is passed through comparator 36, LM339 shown in FIG. 3A, to detect when it exceeds a positive or reciprocal negative threshold shown by the threshold lines of FIG. 7A. The operational values for high pass filter 32 and low-pass filter 34 correspond to the respective thresholds illustrated in FIG. 7A.

Figure 3A:
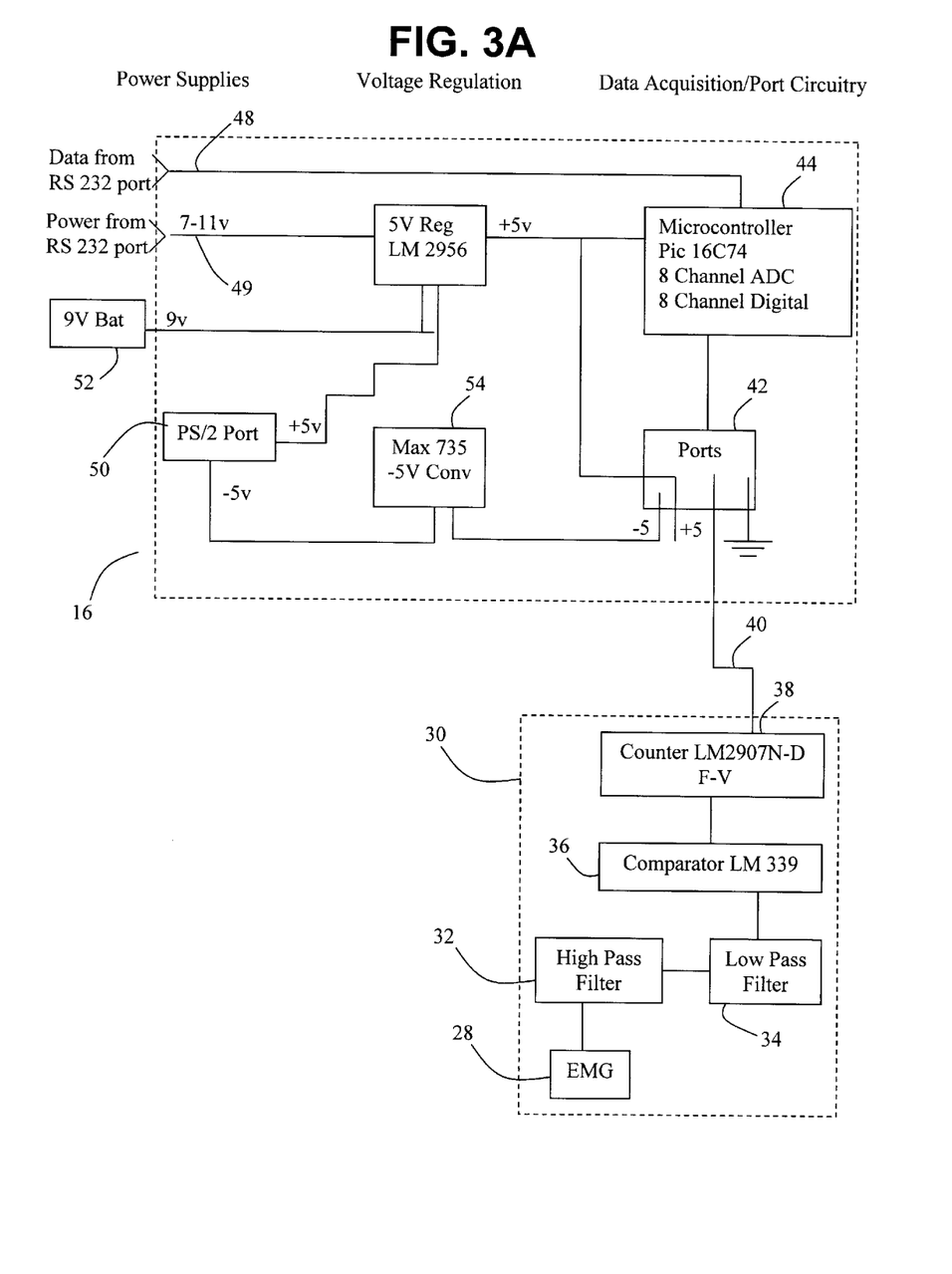
FIGS. 3A and 3B are a schematic diagram of the data acquisition box, microcontroller and a sensor interface constructed in accordance with a preferred embodiment of the invention.
Figure 7B:
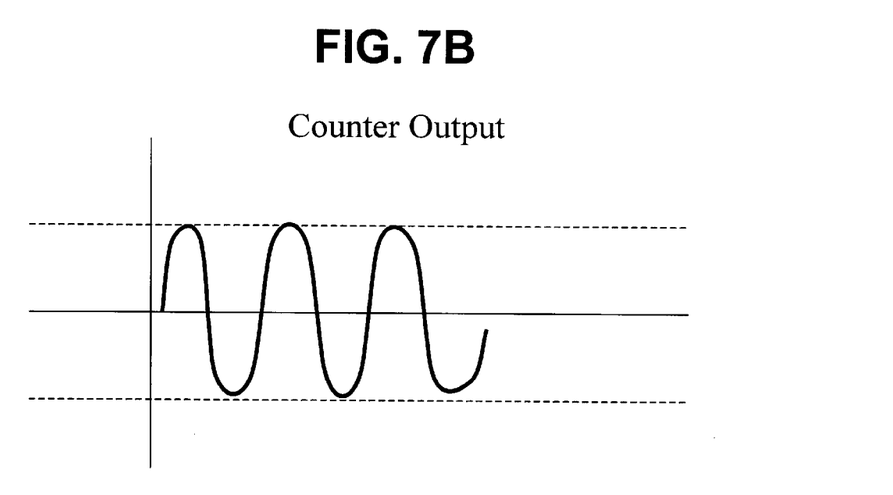

As may be seen in FIG. 3A, counter 38 outputs a pulse, shown in FIG. 7B, whenever the thresholds are exceeded. Also, as the intensity of the detected muscle signal is increased, the frequency of the voltage output increases. As a result, the frequency of the signal pulses at output 40 is increased. Also, noise or minor unintentional user muscle movement, not intended to be input, will be filtered, because either threshold will not be exceeded. Hence, using inexpensive circuitry, EMG sensor 28 output is analyzed in its analog state to detect user input.

It should be appreciated that muscle signals increase in amplitude and frequency when contracted. The problem with muscle amplitude, is that it changes over time and from person to person, and from muscle to muscle. Thus utilizing amplitude and frequency alone would generate too many variables. Applicants have found that by taking a signal and counting the times it crosses the threshold, i.e., to do a rough estimate of frequency content, is a much better approximation which does not have significant variation. In this way, a signal from the quads, although large in amplitude, will have similar frequency characteristics to a facial muscle, very small in amplitude. Therefore, in applicant's system, the output analog signal will be similar and would not need correction for input signal amplitude. This is a significant improvement over prior art techniques.

This user input is then provided to data acquisition box 16. FIG. 3A illustrates the general layout of the data acquisition box (DAQ) 16. All input signals from sensors 14 are sent to DAQ 16 through a port 42. In a preferred embodiment, port 42 is a serial port. It should be appreciated that port 42 may be any type of input port. Examples of input ports include, but are not limited to: serial ports, parallel ports, SCCI ports, universal serial bus ports (USB), infra-red ports (IR) and high frequency ports.

Figure 3B:
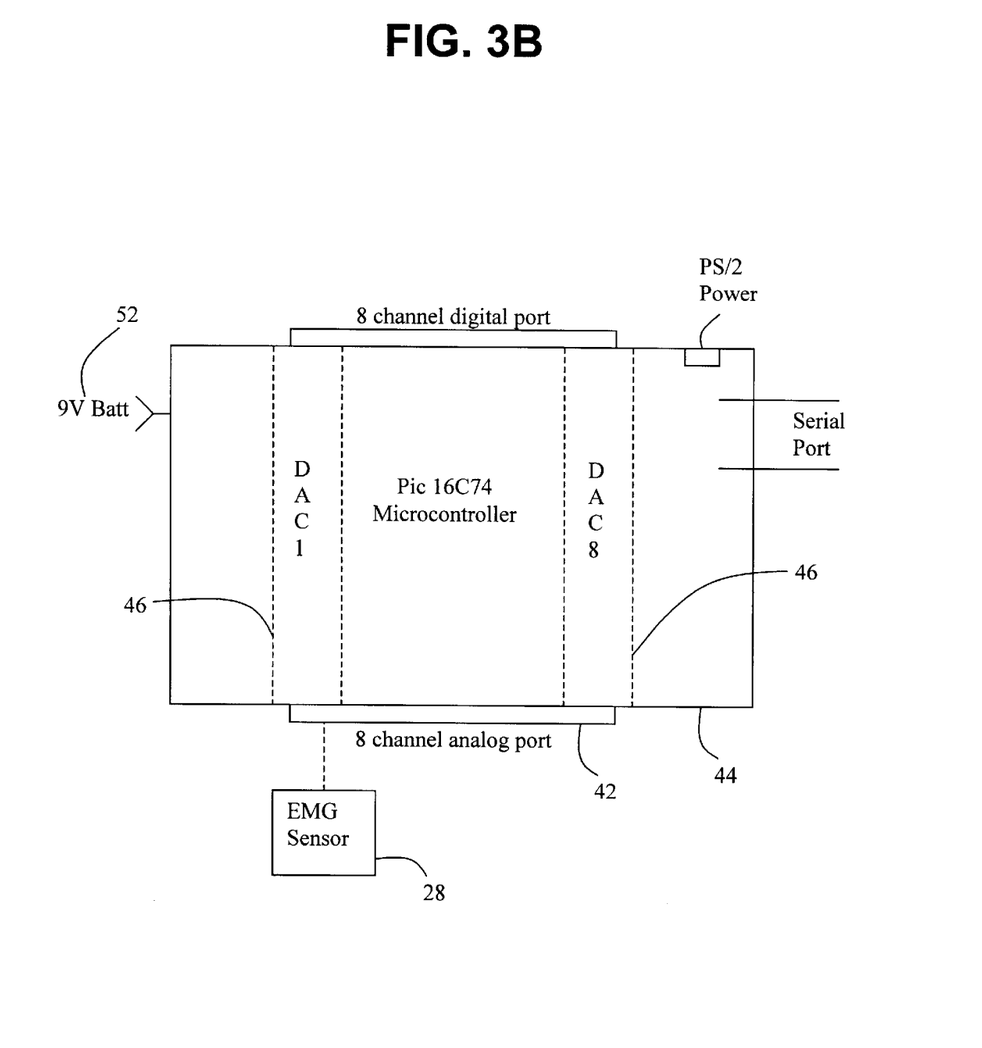

In a preferred embodiment shown in FIGS. 3A and 3B, DAQ 16 uses a PIC16C74 microcontroller 44. Microcontroller 44 is provided with an eight-channel analog to digital converter 46, with variable sampling rates from approximately 200 Hz (8 channel) to approximately 1500 Hz (I channel) and eight-channel digital (button) inputs. Power sources for DAQ 16 include a RS232 port 48, for basic operation, and a PS/2 port 50 and/or batteries 52. In a preferred embodiment, battery 52 is a 9 V source for allowing use of sensors 14 that require more power. Additionally, a 5 volt to −5 volt converter 54 is provided. Thus, DAQ 16 may power basic sensors 14 on its own. Tuning now to FIG. 3B, the connections to microcontroller 44 are illustrated as discussed above.

Figure 2:
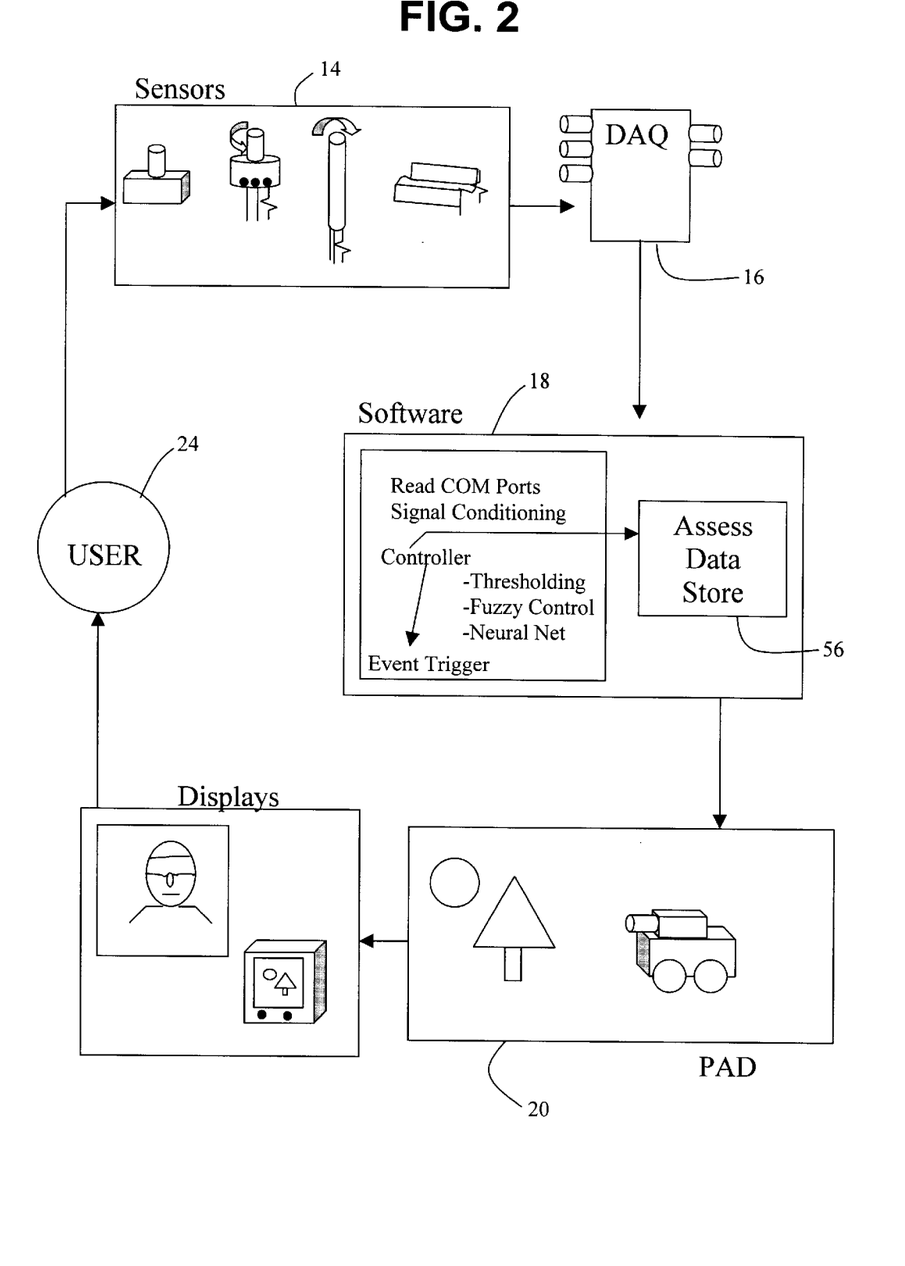
FIG. 2 is a more detailed block diagram of the system of FIG. 1.

We will now discuss software 18 with respect to FIGS. 2, 3A and 3B. The primary purposes of the software are to 1) condition the data received, 2) store the conditioned data and/or raw data, 3) determine if a triggering event has occurred, 4) communicate information to the PAD 20. Freely downloadable software called NeatTools (NT) is used to map user inputs to functionality while assessing and processing user input. NT is a modular interfacing/prototyping package, developed as a visual based run-time program, and uses blocks of functions called "modules." NT allows the user to quickly link several I/O peripherals using ready or custom created modules. NT files receive signals from DAQ 16 through serial port 48. NT then modifies and links these signals to a parallel port 42 for output. NT also reads the inputs from any other input port 42.

The signals are then conditioned through filtering, averaging, and/or calibrating. The data is then stored in a database 56 for subsequent evaluation. Evaluation may include analyzing the frequency and amplitude of the collected data, the timing of the data, and the occurrence of specific events in the data steam. In addition to being stored, the data is sent to microcontroller 44 that maps the inputs 40 to events that are then triggered. Mapping techniques may include thresholding, fuzzy rules, and/or neural networks.

Figure 5A:
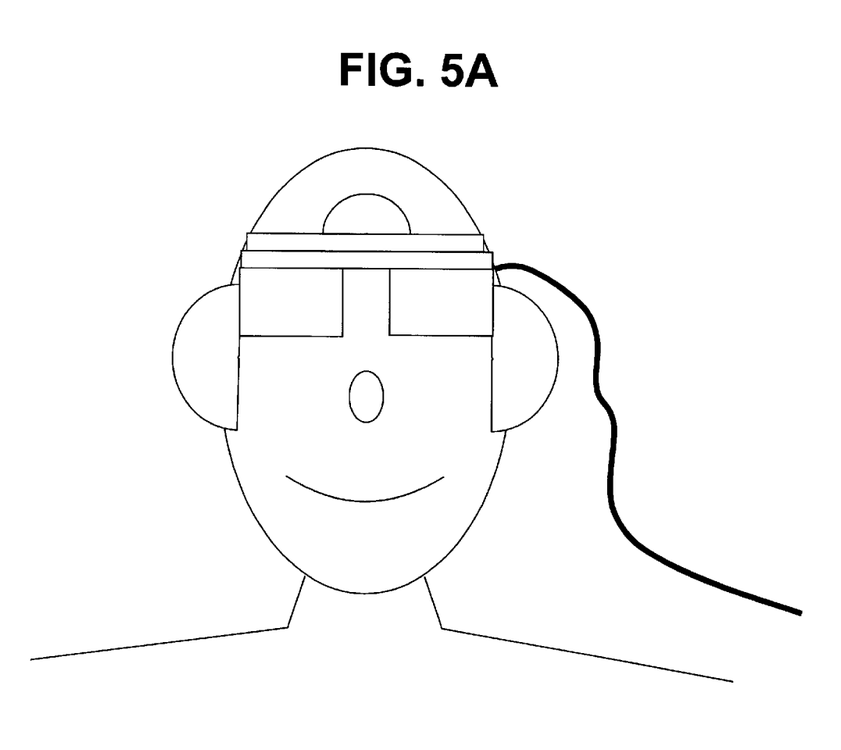
FIGS. 5A and 5B are examples of virtual reality devices connected to personal augmentation devices that may be used in conjunction with the invention.
Figure 5B:
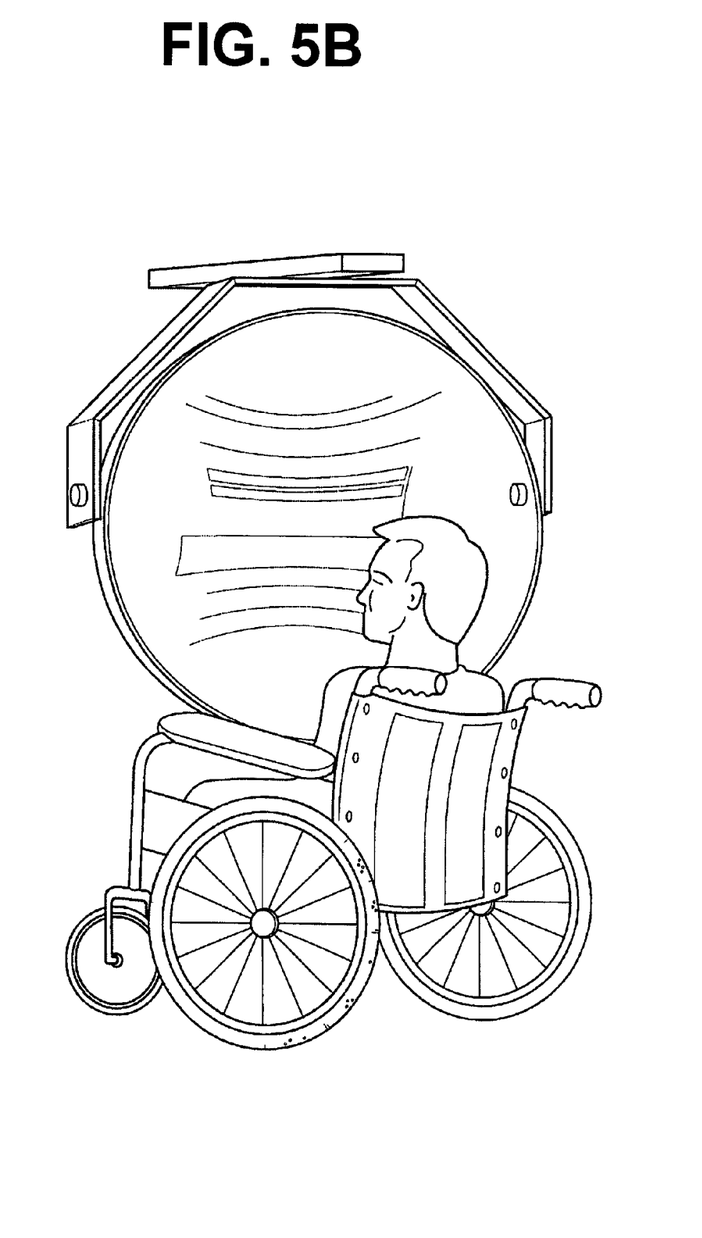

Through mapping, user 24 input 12/14 is mapped to a personal augmentation device (PAD) 20 that acts on the environment for user 24. Examples of PADs 20, that may include, but are not limited to: remote controlled cars, wheelchairs, and/or robots or other controllable devices. In addition, in one embodiment, virtual reality may be used to provide feedback to the user using devices shown in FIGS. 5A and 5B.

Figure 4:
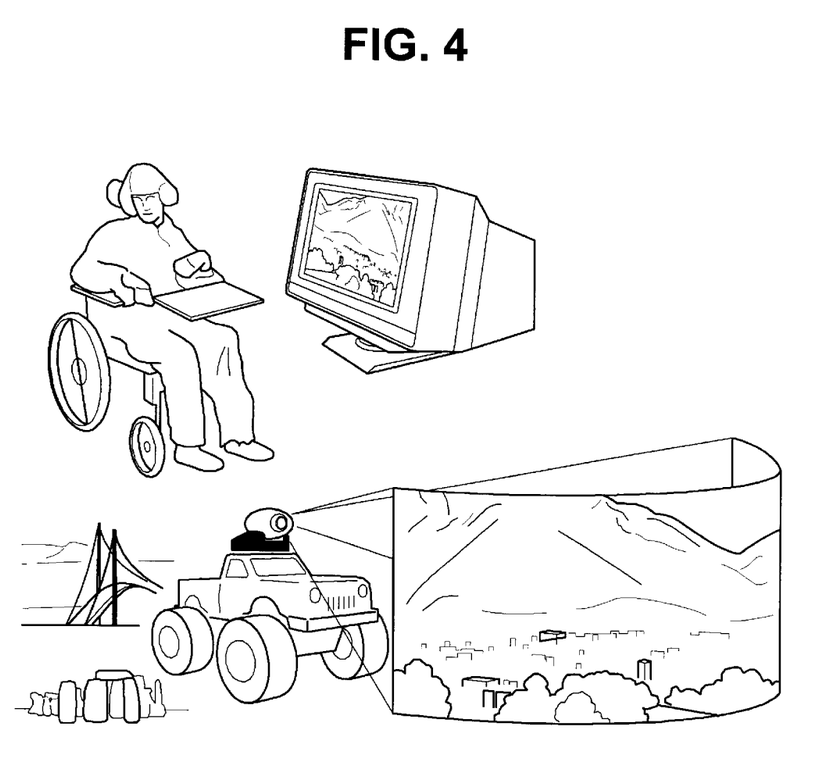
FIG. 4 is a remotely controlled car manipulated by a severely disabled child using the system illustrated in FIGS. 1, 3A and 3B.

The user must interpret this information as being mapped to his or her inputs and continue to respond. The preferred embodiment of this human-technology interface is through virtual reality. Virtual Reality (VR) enables the user of system to receive three-dimensional data to act upon. Other forms of feedback may be accomplished by using a display or other two-dimensional visual feedback. As shown in FIG. 4, a camera may be mounted to a remote-control car 20 that is controlled by user 24. As remote-controlled car 20 is moved around by user 24, interaction between car 20 and the environment is fed back to user 24 using a camera and a display or other two-dimensional visual feedback. The output of the camera or similar devices may be provided using a two-dimensional or three-dimensional virtual environment. The goal of introducing VR is to increase the transfer of information between user 24 and the environment. We define VR as an interactive set of tools that fuse the user with the system. These tools allow the user to engage their environment in a unique way and use their imagination to interrogate their environment. VR allows the user to take advantage of the relationships between physical stimuli and the cognitive impact from this stimulus.

One use of VR in system 10 is the introduction of three-dimensional displays. Commonly referred to as VR goggles, shown in FIG. 5A, this technology incorporates high fidelity, stereoscopic visual display with stereo sound. The images and sounds captured by PAD 20 are presented to user 24 in such a way that user 24 would have a great sense of being where PAD 20 is. Another VR, display system is comprised of a dome, shown in FIG. 5B that user 24 sits in or under. Three-dimensional images surround user 24. Positioning systems allow user 24 to rotate their head in space that may be mapped to the movement of remote camera 20 or the motion of remote car 20 to navigate the environment.

Another use of VR is haptic (touch) interaction. The human haptic system is unique in that it is bi-directional. Touch refers to both sensing and acting upon an environment. Introduction of haptic joysticks 12 presents the user with force and vibro-tactile feedback. If PAD 20 were to hit an obstacle user 24 would feel the obstacle as the joystick would not move forward. As PAD 20 transits over rough terrain haptic joystick 12 would vibrate and shake for user 24. Haptic chairs simulate movement of PAD 20 allowing user 24 to imagine they are traveling on PAD 20.

Figure 6:
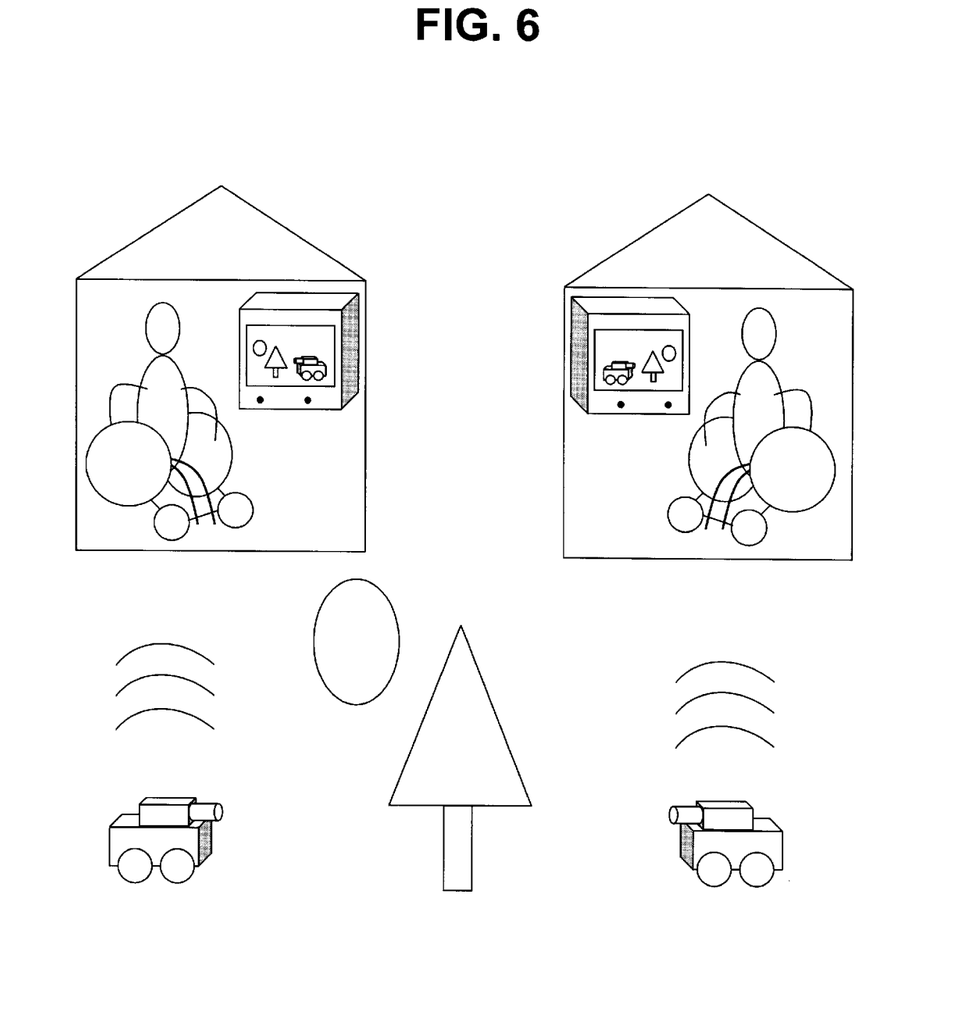
FIG. 6 illustrates an alternate embodiment of the invention where a user interacts with another PAD of the same or different type.

FIG. 6 discloses a collaborative tele-presence embodiment where two systems are simultaneously used to provide non-static interaction between two users 24. Multiple users 24 may interact through remote PADs 20. The remote PADs 20 may be implemented through hardware, as shown in the Figure or through software such that users 24 are interacting in a virtual environment through an interface such as the Internet. The advantage of collaboration is to provide the dynamic interaction with other individuals for the purpose of play, therapy, education or skill development.

It should be appreciated that the above embodiments have primarily addressed analog systems. The teachings of the present invention may also be extended to digital embodiments without departing from the scope of the present invention.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method of evaluating and training for the development of cognitive, functional and perceptual skills, comprising:

detecting the input of a user with one or more sensors, wherein said one or more sensors comprises one or more EMG sensors to detect movement of said user;

mapping the input of said user to controls of a personal augmentation device by a microcontrolled data acquisition box;

analyzing the output of said EMG sensor using a comparator and a counter; and producing a pulsed output indicative of said detected movement of said user.

2. The method recited in claim 1, further comprising the steps of:

conditioning said input through filtering, averaging, and/or calibrating to generate modified data;

storing said modified data in a database for subsequent evaluation; and evaluating said modified data by analyzing characteristics of said data for occurrence of specific events in said modified data.

3. The method recited in claim 1, further comprising the step of:

providing feedback to said user from said personal augmentation device.

4. A system for evaluating and training for the development of cognitive, functional and perceptual skills, said system comprising:

one or more sensors for generating input data;

data acquisition means for acquiring said input data;

mapping means for mapping said input data to controls of a personal augmentation device; and feedback means for providing environmental conditions of said personal augmentation device to a user.

5. A system for evaluating and training for the development of cognitive, functional and perceptual skills, said system comprising:

one or more sensors for generating input data;

data acquisition means for acquiring said input data; and mapping means for mapping said input data to controls of a personal augmentation device, wherein said mapping means comprises signal conditioning means for conditioning said input data to generate modified data, storing means for storing said modified data in a database for subsequent evaluation, and evaluating means for evaluating said modified data by analyzing characteristics of said data for occurrence of specific events in said modified data.

6. A system for evaluating and training for the development of cognitive, functional and perceptual skills, said system comprising:

one or more sensors for generating input data, wherein said one or more sensors comprises one or more EMG sensors to detect movement of said user;

data acquisition means for acquiring said input data;

mapping means for mapping said input data to controls of a personal augmentation device;

analyzing the output of said EMG sensor using a comparator and a counter; and producing a pulsed output indicative of said detected movement of said user.

7. A system for evaluating and training for the development of cognitive, functional and perceptual skills, said system comprising:

one or more sensors for generating input data;

data acquisition means for acquiring said input data;

mapping means for mapping said input data to controls of a personal augmentation device, conditioning means for conditioning said input through filtering, averaging, and/or calibrating to generate modified data;

storing means for storing said modified data in a database for subsequent evaluation; and evaluating means for evaluating said modified data by analyzing characteristics of said data for occurrence of specific events in said modified data.

* * * * *